(12) United States Patent
Cao et al.

(10) Patent No.: US 8,303,510 B2
(45) Date of Patent: Nov. 6, 2012

(54) MEDICAL IMAGING DEVICE HAVING A FORWARD LOOKING FLOW DETECTOR

(75) Inventors: Pei Jei Cao, Fremont, CA (US); Jian R. Yuan, Hayward, CA (US); Richard Romley, Tracy, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 633 days.

(21) Appl. No.: 11/173,548

(22) Filed: Jul. 1, 2005

(65) Prior Publication Data
US 2007/0016054 A1     Jan. 18, 2007

(51) Int. Cl.
*A61B 8/14* (2006.01)
(52) U.S. Cl. ....................................................... 600/466
(58) Field of Classification Search .................... 600/466
See application file for complete search history.

(56) References Cited

U.S. PATENT DOCUMENTS

| | | | |
|---|---|---|---|
| 4,601,292 A * | 7/1986 | Fidel et al. | 600/453 |
| 5,000,185 A | 3/1991 | Yock | |
| 5,156,050 A * | 10/1992 | Schmid et al. | 73/628 |
| 5,203,337 A | 4/1993 | Feldman | |
| 5,211,176 A * | 5/1993 | Ishiguro et al. | 600/463 |
| 5,321,501 A | 6/1994 | Swanson et al. | |
| 5,361,768 A | 11/1994 | Webler et al. | |
| 5,368,035 A | 11/1994 | Hamm et al. | |
| 5,373,849 A | 12/1994 | Maroney et al. | |
| 5,421,338 A | 6/1995 | Crowley et al. | |
| 5,437,282 A | 8/1995 | Koger et al. | |
| 5,598,845 A * | 2/1997 | Chandraratna et al. | 600/459 |
| 5,680,865 A | 10/1997 | Tanaka | |
| 5,928,153 A * | 7/1999 | Chiang et al. | 600/454 |
| 6,048,323 A * | 4/2000 | Hon | 600/588 |
| 6,078,831 A | 6/2000 | Belef et al. | |
| 6,450,964 B1 | 9/2002 | Webler | |

(Continued)

FOREIGN PATENT DOCUMENTS

| | | |
|---|---|---|
| JP | 04-183456 A | 6/1992 |
| WO | 97/32182 | 9/1997 |
| WO | 97/32277 | 9/1997 |

OTHER PUBLICATIONS

Huang et al., "Optical Coherence Tomography," Science, 254, Nov. 22, 1991, pp. 1178-1181.

*Primary Examiner* — Brian Casler
*Assistant Examiner* — Saurel J Selkin
(74) *Attorney, Agent, or Firm* — Frommer Lawrence & Haug LLP; Patrick R. Turner

(57) ABSTRACT

The present invention generally relates to medical devices, and more particularly to an improved medical imaging device. In one embodiment, an imaging device includes a drive shaft having proximal and distal ends received within the lumen; an imaging transducer coupled to the distal end of the drive shaft and positioned at the distal portion of the elongate member; and a flow detector coupled to the imaging transducer. The flow detector may include a forward facing ultrasound transducer configured to emit energy in the direction of the longitudinal axis of the imaging device and detect a Doppler shift in the received echoes. In the case where the imaging device is located in a vessel having blood flow, such information may be used to calculate the velocity of the blood flow. The imaging device may be configured to be located in a catheter or guidewire.

23 Claims, 5 Drawing Sheets

U.S. PATENT DOCUMENTS

| | | |
|---|---|---|
| 6,524,249 B2 | 2/2003 | Moehring et al. |
| 6,740,040 B1 * | 5/2004 | Mandrusov et al. ........... 600/439 |
| 2002/0007120 A1 * | 1/2002 | Moore et al. .................. 600/466 |
| 2002/0193690 A1 | 12/2002 | Moore |
| 2003/0149366 A1 * | 8/2003 | Stringer et al. ................ 600/464 |
| 2004/0073204 A1 * | 4/2004 | Ryan et al. ....................... 606/27 |
| 2004/0116800 A1 * | 6/2004 | Helfer et al. ................... 600/411 |
| 2004/0122448 A1 * | 6/2004 | Levine .......................... 606/139 |

\* cited by examiner

MEDICAL IMAGING DEVICE HAVING A FORWARD LOOKING FLOW DETECTOR

FIELD OF THE INVENTION

The field of the invention relates to medical devices, and more particularly to medical imaging devices for placement in catheters and guidewires.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer. These are generally known in the art as Intravascular Ultrasound ("IVUS") devices.

FIG. 1 shows an example of an imaging transducer assembly 1 known in the art. The imaging transducer 1 is typically within the lumen 10 of a guidewire or catheter (partially shown), having an outer tubular wall member 5. To obtain an image of a blood vessel the imaging transducer assembly 1 may be inserted into the vessel. The transducer assembly 1 may then interrogate the cross-sectional plain of the vessel from the inside by rotating while simultaneously emitting energy pulses, e.g., ultrasound pulses, and receiving echo signals.

It may be desirable to obtain not only a cross-sectional plane of the vessel, but also information on blood flow within the vessel. Accordingly, an improved imaging catheter would be desirable.

SUMMARY OF THE INVENTION

The present invention generally relates to medical devices, and more particularly to an improved medical imaging device. In one embodiment, an imaging device includes a drive shaft having proximal and distal ends received within the lumen; an imaging transducer coupled to the distal end of the drive shaft and positioned at the distal portion of the elongate member; and a flow detector coupled to the imaging transducer. The flow detector may include a forward facing ultrasound transducer configured to emit energy in the direction of the longitudinal axis of the imaging device and detect a Doppler shift from the received echoes. The imaging device may be configured to be placed in a catheter or guidewire.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
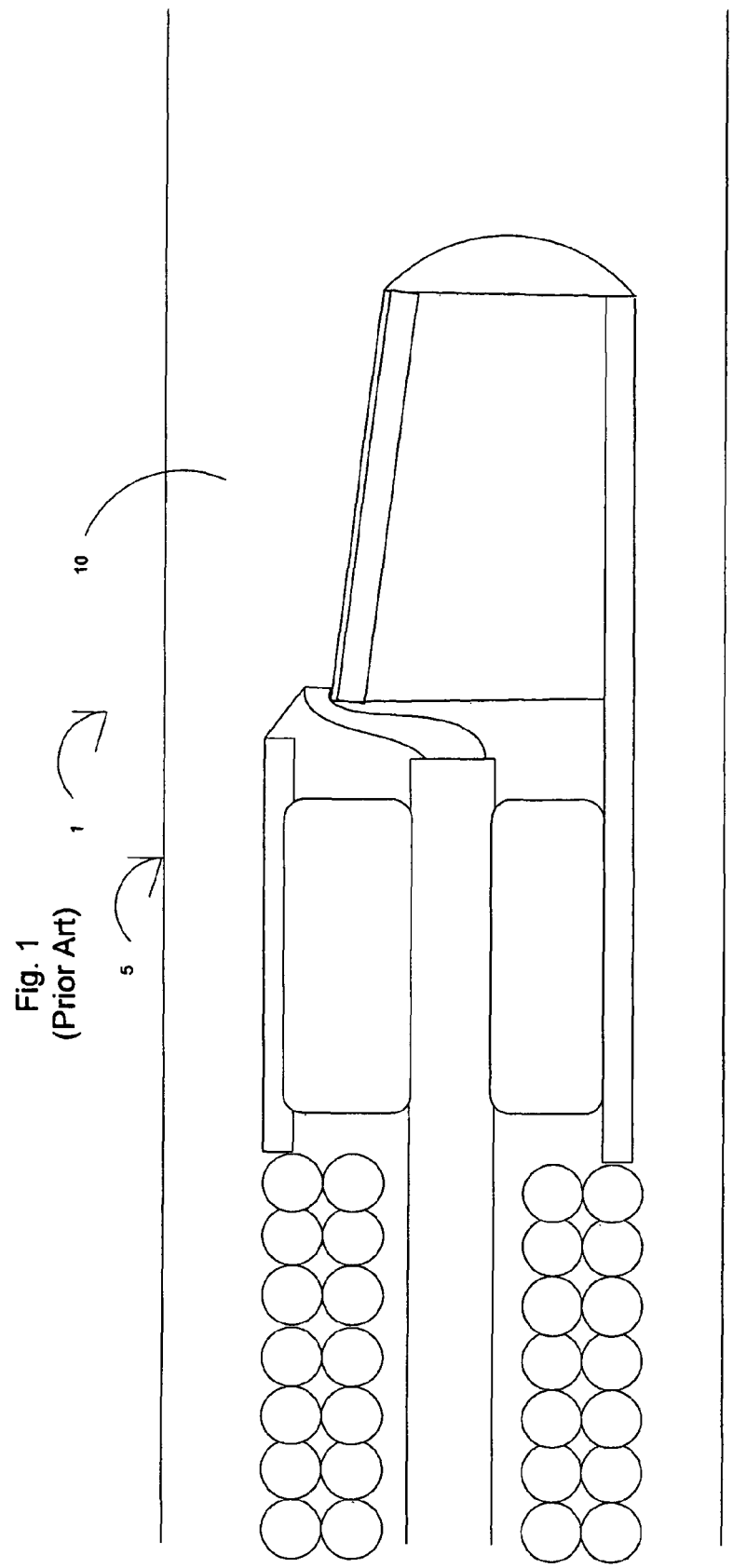
FIG. 1 is a cross-sectional side view of an imaging transducer assembly known in the art.
Figure 2:
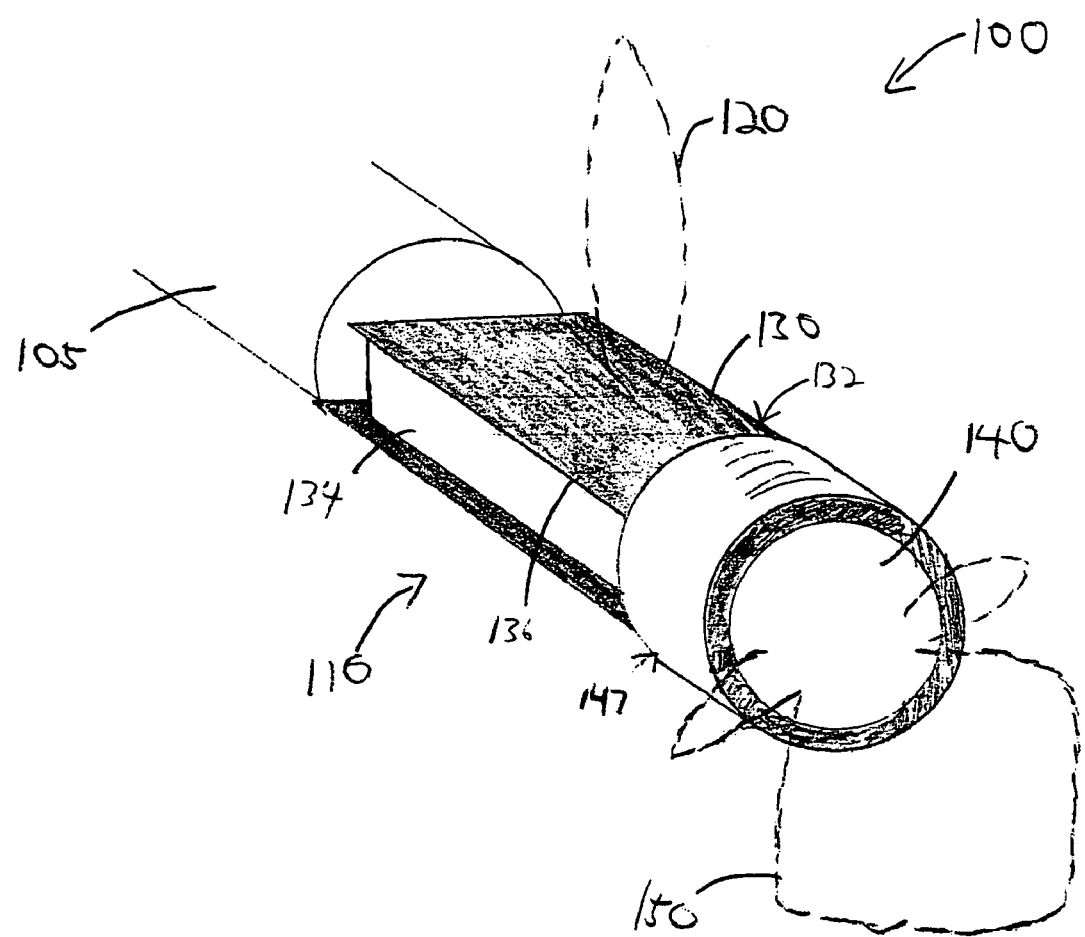
FIG. 2 is a perspective view of an imaging device in accordance with a preferred embodiment of the present invention.

Turning to FIG. 2, an imaging device 100 is shown in accordance with a preferred embodiment of the present invention. The imaging device 100 includes a transducer housing 110 having an imaging transducer 130 known in the art, such as that shown in FIG. 1. In the case where the imaging transducer 130 is an ultrasound transducer, the transducer 130 may include a layer of electrode coated piezoelectric crystal ("PZT") 136, "sandwiched" between a conductive acoustic lens 132 and a conductive backing material 134, formed from an acoustically absorbent material (e.g., an epoxy substrate having tungsten particles). During operation, the PZT layer 136 is electrically excited by both the backing material 134 and the acoustic lens 132, causing energy, e.g., acoustic pulses 120, to be emitted from the lens 132, which faces a direction generally perpendicular to the longitudinal axis of the imaging device 100. As described above, a cross-sectional image of a vessel may be obtained from the imaging transducer 130 as it rotates about the longitudinal axis of the imaging device 100.

The transducer 130 is coupled to the distal end of a cable 105 that includes a drive shaft (not shown) and conductors (not shown) that electrically couple the transducer 130 to a processing unit (not shown). An additional transducer 140 is coupled to the distal end of the imaging transducer 130. The additional transducer 140 may be positioned within a housing socket 147 that is mounted to the distal end of the imaging transducer 130. The additional transducer 140 is forward facing, i.e., the transducer 140 faces a direction generally parallel to the longitudinal axis of the imaging device 100. The additional transducer 140, herein referred to as the Doppler transducer 140, can be configured to send narrow band burst energy signals, e.g., acoustic signals, and receive the echoes. From the received echoes, the velocity of blood flow within a vessel may be calculated. Due to the red cell's movement in the blood, the emitted energy signals scatter, resulting in scattered echoes. The scattered echoes will have a frequency shift from the original signals, known in the art as a Doppler shift. Generally, the Doppler shift is proportional to the blood velocity and cosine of the Doppler angle, which is the angle between the blood flow and the energy beam, e.g., ultrasound beam. For ultrasound beams, the Doppler shift can be within audio range, so a user can determine the direction of blood flow by listening for the Doppler shift. Such information, i.e., direction and velocity of the blood flow, is invaluable in locating and evaluating the existence or effect of stenosis in a patient.

In the case where the Doppler transducer 140 is an ultrasound transducer 140, the Doppler frequency shift information can be detected by using demodulation methods on the received echoes. The Doppler frequency shift $f_d$ is quantitatively related to the blood velocity that it encounters:

$$f_d = \frac{2v\cos\theta}{c} f_0, \quad (1)$$

where $f_0$ is the center frequency of the transmitted acoustic beam emitted from the Doppler transducer 140, c is the sound velocity in the tissue, v is the velocity of the blood flow, and θ is the angle between the flow of the blood and the ultrasound beam 150. Equation (1) shows that the Doppler shift has a maximum value when the Doppler transducer 140 is parallel to the blood flow direction, i.e., cos 0°. Thus, the Doppler transducer 140 can serve as a forward-facing guide for the imaging catheter or guidewire. The user can simply search for the Doppler shift. Such a transducer 140 may include a thin PZT layer, similar to the ultrasound transducer described above. Other single crystal and/or piezofilm materials may be used, or any kind of composite materials using piezomaterials. The transducer 140 may be a single beam, an annular array, or multi-beam device.

Further, other imaging devices may be used, instead of, or in addition to imaging transducers 130, such as light based apparatuses for obtaining images through optical coherence tomography (OCT). Image acquisition using OCT is described in Huang et al., "Optical Coherence Tomography," Science, 254, Nov. 22, 1991, pp 1178-1181, which is hereby incorporated by reference in its entirety. A type of OCT imaging device, called an optical coherence domain reflectometer (OCDR) is disclosed in Swanson U.S. Pat. No. 5,321,501, which is incorporated herein by reference. The OCDR is capable of electronically performing two- and three-dimensional image scans over an extended longitudinal or depth range with sharp focus and high resolution and sensitivity over the range. In addition, other devices may be used instead of, or in addition to, ultrasound transducers 140, such as light based apparatuses.

The Doppler transducer 140 may have a beam pattern 150 that is wider than the imaging transducer 130. Further, because the Doppler transducer's 140 surface is generally perpendicular to the longitudinal axis of the imaging device 100, the rotation of the imaging device 100 and/or the imaging transducer 130 will have little effect on the Doppler shift signal, which is generally only sensitive to the relative movement between the Doppler transducer 140 and the scattered echoes.

Where ultrasound transducers are used for the imaging transducer 130 and the Doppler transducer 140, the Doppler transducer 140 can operate at a relatively narrow bandwidth, different from the imaging transducer 130, allowing both the transducers 130 and 140 to operate in parallel. For example, the imaging transducer 130 may operate at 40 MHz with a bandwidth of 80%, i.e., where the low frequency band edge will be at 24 MHz. In such a case, a Doppler transducer 140 may operate at 20 MHz. Assuming a maximum flow velocity for the blood is approximately 1 meter per second (m/s) and the sound velocity is approximately 1500 m/s, from equation (1), the maximum Doppler shift is lower than 26 kHz. Thus, in the frequency domain, the two signals, i.e., the imaging signals, and the Doppler signals, are substantially different.

Preferably, for efficiency purposes, the electrical impedance between the imaging transducer 130 and the Doppler transducer 140 are configured to be different. Thus, one of the transducers 130 and 140 is configured to have a high impedance at the operating frequency of the other transducer 130 and 140, and the operating energy will travel to the corresponding load. With inductor tuning methods known in the art, the imaging transducer 130 can have an impedance as high as 1 kΩ at 20 MHz and the Doppler transducer 140 can have an impedance of 370Ω at 40 MHz.

Figure 3A:
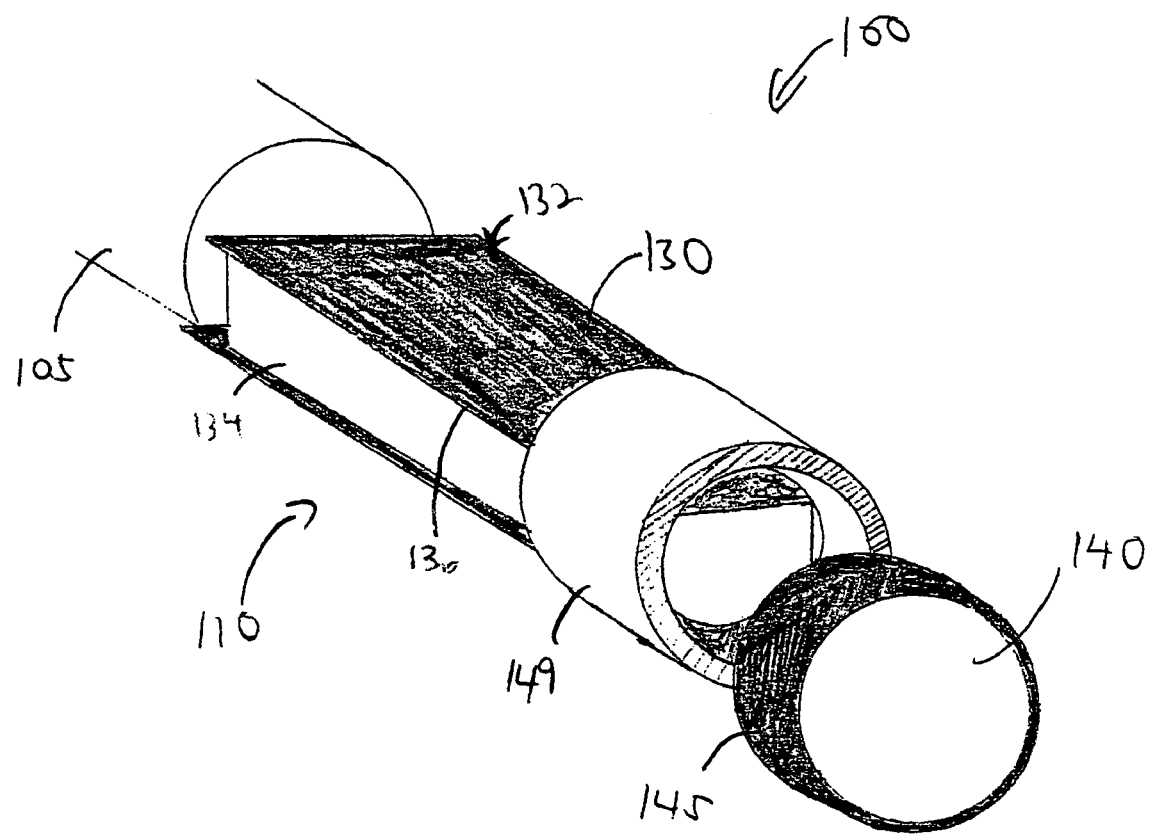
FIG. 3a is a perspective view illustrating a construction of an imaging device in accordance with a preferred embodiment of the present invention.

To construct an imaging device 100 having both an imaging transducer 130 and a Doppler transducer 140, a round socket 149 is attached to the distal end of the imaging transducer 130 and configured to receive the Doppler transducer 140, which is covered in an isolation ring 145, as shown in FIG. 3a. The round socket 149 functions as a housing for the Doppler transducer 140. The round socket 149 can be conductive, serving as a ground for both transducers 130 and 140. A signal wire for the Doppler transducer 140 (not shown) can be directly connected from the imaging transducer surface 130 or be located on the side of the imaging transducer 130. Of course, the shape and size of the socket 149 need not be round as the socket should be adapted to accommodate the shape and size of the Doppler transducer 140.

Figure 3B:
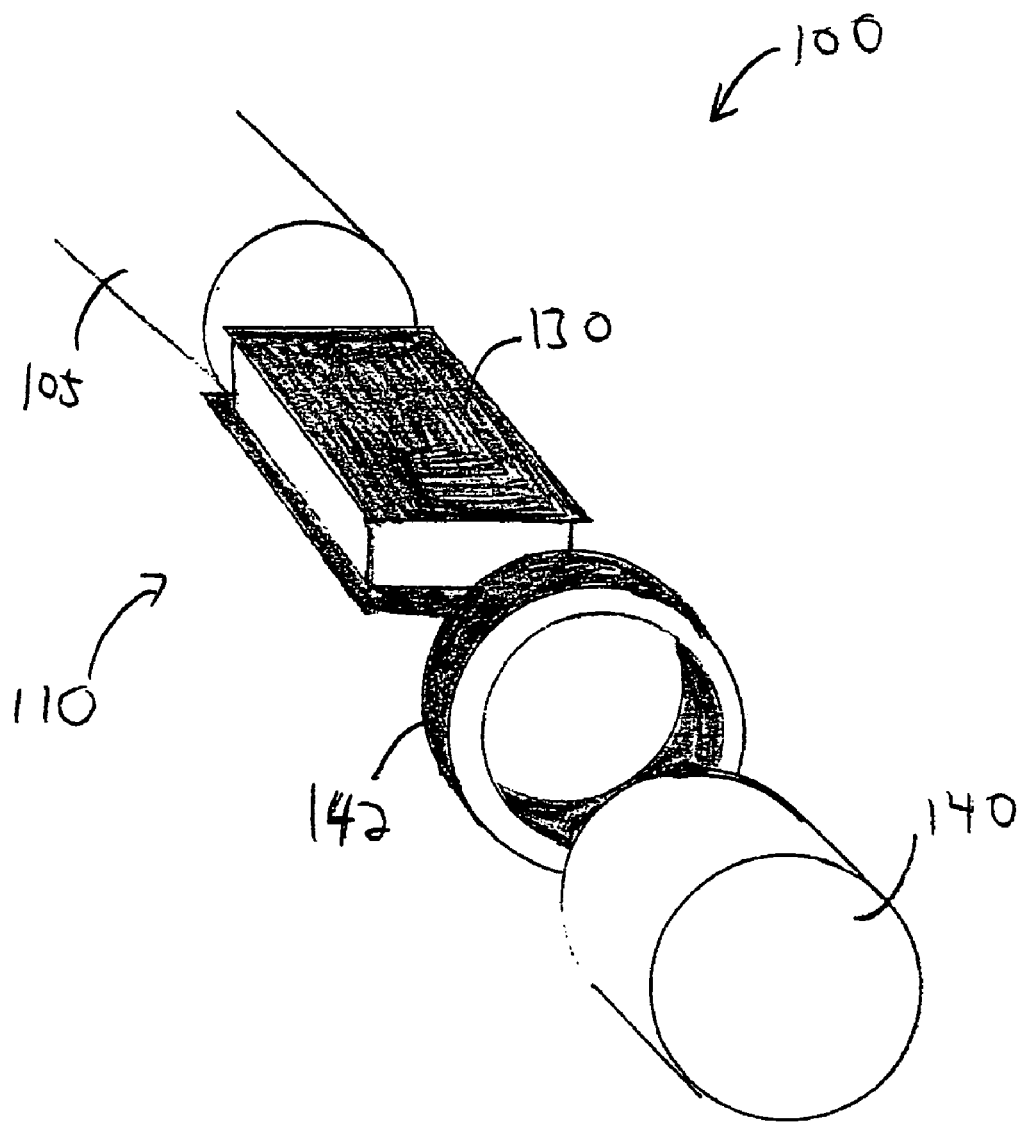
FIG. 3b is a perspective view illustrating an construction of an imaging device in accordance with a preferred embodiment of the present invention.

In another embodiment, an isolation ring 142 configured to cover the Doppler transducer 140 can be constructed to also function as the housing, as shown in FIG. 3b. The isolation ring 142 and the Doppler transducer 140 may be attached to the imaging transducer housing 110 with conductive epoxy. The Doppler transducer 140 may have any shape, such as round, square, hexagon, or octagon. Further, to increase the beam 150 diameter of the Doppler transducer 140, the transducer 140 can include a convex surface and/or a separate lens (not shown).

Figure 4:
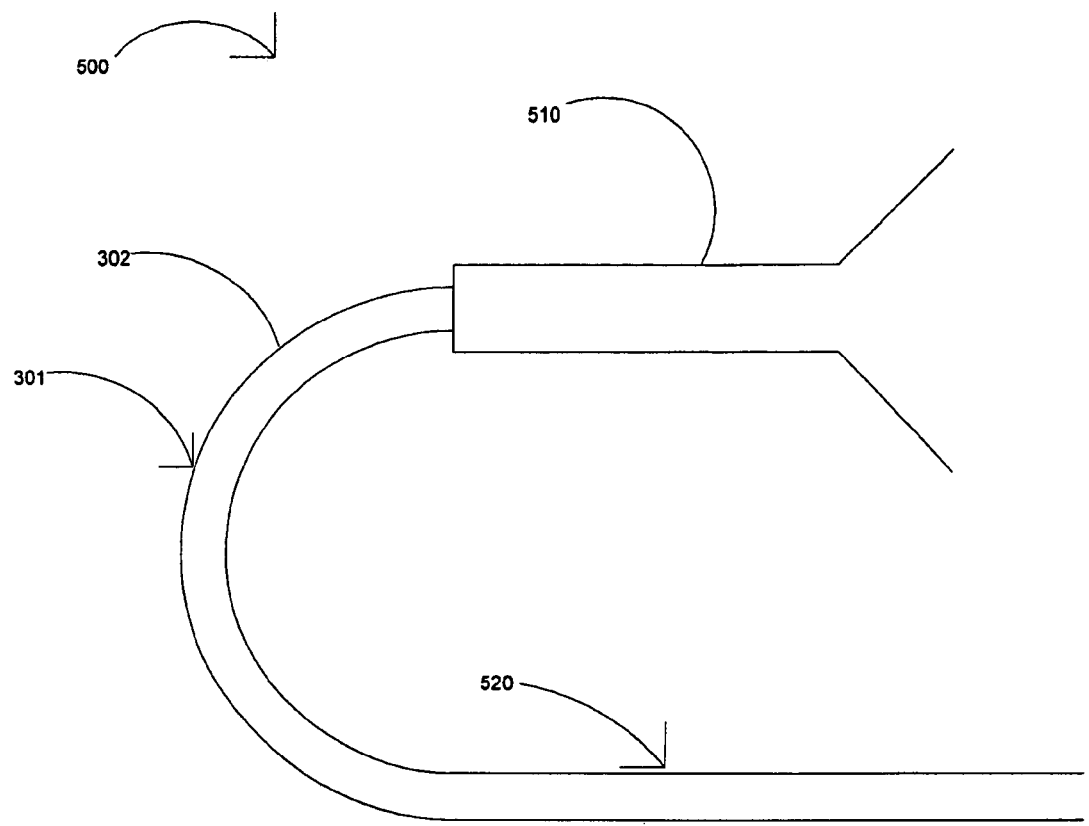
FIG. 4 is a cross-sectional view of an imaging wire in accordance with a preferred embodiment of the present invention.

Turning to FIG. 4, the imaging device 100 may be used in a catheter, as described above, and can also be placed in a distal portion 520 of a guidewire 500. The guidewire 500 may comprise a guidewire body 302 in the form of a flexible, elongate tubular member, having an outer wall 301. The guidewire body 302 may be formed of any material known in the art including nitinol hypotube, metal alloys, composite materials, plastics, braided polyimide, polyethylene, peek braids, stainless steel, or other superelastic materials.

The Doppler transducer 140 and the imaging transducer 130 may utilize two different wiring systems for electrical coupling to one or more processing devices (shown below). For example, the cable 105 attached to the proximal end of the imaging transducer 130 may include two coaxial cables, each servicing a transducer 130 and 140. Alternatively, the coupling may be indirect, capacitive, or inductive coupling as known in the art.

Figure 5:
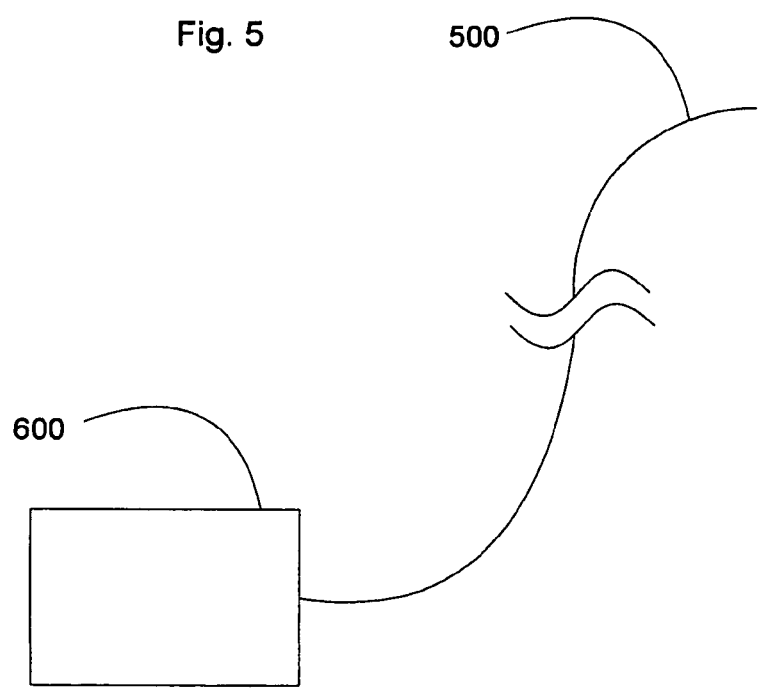
FIG. 5 is a diagram of a medical imaging system in accordance with a preferred embodiment of the present invention.

Turning to FIG. 5, a proximal portion 510 of the guidewire 500, shown in FIG. 4, may be adapted to connect to circuitry 600 that processes imaging signals from the imaging transducer 130 and/or electrical signals from the Doppler transducer 140, such circuits being well known.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An imaging device configured to be located in an imaging catheter, the imaging device having a longitudinal axis, said imaging device comprising:
    a drive shaft having proximal and distal ends;
    an imaging transducer coupled to the distal end of the drive shaft, the imaging transducer configured and arranged to transmit acoustic signals at a first frequency and with a bandwidth including the first frequency, wherein the imaging transducer faces perpendicular to the longitudinal axis of the imaging device and is rotatable about the longitudinal axis of the imaging device;
    an ultrasound Doppler transducer coupled to a distal end of the imaging transducer and configured and arranged such that rotation of the imaging transducer causes a corresponding rotation of the ultrasound Doppler transducer, the Doppler transducer configured and arranged to operate concurrently with the imaging transducer, the Doppler transducer configured and arranged to transmit acoustic signals at a second frequency, wherein the bandwidth of the imaging transducer does not overlap with the second frequency of the Doppler transducer, wherein the ultrasound Doppler transducer faces a direction that is parallel to the longitudinal axis of the imaging device; and
    an isolation ring coupled to and surrounding the Doppler transducer.

2. The imaging device of claim 1, wherein the Doppler transducer is positioned adjacent to the imaging transducer.

3. The imaging device of claim 1, wherein the imaging transducer is an ultrasound transducer.

4. The imaging device of claim 1, wherein the drive shaft includes a first coaxial cable coupled to the imaging transducer and a second coaxial cable coupled to the Doppler transducer.

5. The imaging device of claim 1, wherein the Doppler transducer has an energy emitting surface that is circular.

6. The imaging device of claim 1, wherein the Doppler transducer is an annular array.

7. The imaging device of claim 1, wherein the imaging device is configured to be located within a blood vessel having blood flow, and the Doppler transducer is configured to provide information enabling a calculation of a velocity of the blood flow.

8. The imaging device of claim 1, wherein the imaging device is configured to be located within a blood vessel having blood flow, and the Doppler transducer is configured to indicate a direction of the blood flow.

9. The imaging device of claim 1, further comprising a socket coupled to and surrounding the isolation ring.

10. The imaging device of claim 9, wherein the socket is formed from a conductive material.

11. The imaging device of claim 9, wherein the socket is disposed over the ultrasound Doppler transducer and the isolation ring such that the socket does not cover the imaging transducer.

12. An imaging catheter configured to be deployed within a blood vessel having blood flow, the imaging catheter comprising:
    an elongate member having proximal and distal portions, a longitudinal axis, and a lumen extending along the longitudinal axis of the elongate member;
    a drive shaft having proximal and distal ends received within the lumen of the elongate member;
    an imaging transducer coupled to the distal end of the drive shaft and positioned at the distal portion of the elongate member, the imaging transducer configured and arranged to operate at a first frequency and with a bandwidth that includes the first frequency, wherein the imaging transducer faces perpendicular to the longitudinal axis of the imaging device and is rotatable about the longitudinal axis of the imaging device;
    a flow detector comprising an ultrasound transducer coupled to a distal end of the imaging transducer, the flow detector configured and arranged to operate at a second frequency, wherein the bandwidth of the imaging transducer does not overlap with the second frequency of the flow detector, wherein the flow detector faces a direction that is parallel to the longitudinal axis of the imaging device, and wherein the flow detector is coupled to the imaging transducer and configured and arranged such that rotation of the imaging transducer causes a corresponding rotation of the flow detector; and
    an isolation ring coupled to and surrounding the ultrasound transducer of the flow detector;
    wherein the imaging transducer and the ultrasound transducer of the flow detector have substantially different electrical impedances while operating simultaneously.

13. The imaging catheter of claim 12, wherein the imaging catheter is configured to be located within a blood vessel having blood flow, and the flow detector is configured to provide information enabling a calculation of a velocity of the blood flow.

14. The imaging catheter of claim 12, wherein the imaging catheter is configured to be located within a blood vessel having blood flow, and the flow detector is configured to indicate a direction of the blood flow.

15. The imaging catheter of claim 12, wherein the imaging catheter is configured to be located within a blood vessel having blood flow, and the flow detector is configured to provide information enabling a calculation of a Doppler shift resulting from sending signals against the blood flow and receiving scattered echoes.

16. The imaging catheter of claim 12, wherein the ultrasound transducer includes a PZT layer.

17. The imaging catheter of claim 12, wherein the drive shaft includes a first coaxial cable coupled to the imaging transducer and a second coaxial cable coupled to the flow detector.

18. The imaging catheter of claim 12, wherein the imaging transducer is an ultrasound transducer.

19. The imaging catheter of claim 12, wherein the imaging transducer is an OCT device.

20. The imaging catheter of claim 12, wherein the flow detector includes an isolation layer surrounding the ultrasound transducer of the flow detector, and a socket surrounding the isolation layer, wherein the socket is coupled to the imaging transducer.

21. The imaging catheter of claim 12, further comprising a transducer housing, wherein the imaging transducer is mounted on the transducer housing and the isolation ring is attached to a distal end of the transducer housing.

22. The imaging catheter of claim 12, wherein the ultrasound transducer of the flow detector is configured to have a high electrical impedance at the operating frequency of the imaging transducer.

23. The imaging catheter of claim 12, wherein the imaging transducer is configured to have a high electrical impedance at the operating frequency of the ultrasound transducer of the flow detector.

* * * * *